United States Patent [19]

Rowe

[11] 4,395,488
[45] Jul. 26, 1983

[54] DRIVE-THROUGH PIT PRODUCTION OF ETHANOL

[76] Inventor: Delton J. Rowe, 1740 Speyer La., Redondo Beach, Calif. 90278

[21] Appl. No.: 301,718

[22] Filed: Sep. 14, 1981

[51] Int. Cl.³ .............................................. C12P 7/06
[52] U.S. Cl. .................................. 435/161; 435/165; 435/287; 435/801; 435/819; 71/10; 48/197 A
[58] Field of Search ............... 435/161, 165, 801, 819, 435/287; 71/8–10; 48/197 A

[56] References Cited

U.S. PATENT DOCUMENTS

| | | | |
|---|---|---|---|
| 4,100,023 | 7/1978 | McDonald | 71/10 X |
| 4,169,712 | 10/1979 | Boyce et al. | 48/197 A |
| 4,242,455 | 12/1980 | Muller et al. | 435/165 X |

Primary Examiner—Ferris H. Lander
Attorney, Agent, or Firm—Vincent L. Carney

[57] ABSTRACT

Ethanol ($C_2H_5OH$) is produced efficiently by employing a drive-through pit in which carbohydrate-containing material is fermented by hydrolyzing agents such as enzymes. The configuration and depth of the pit are such as to permit conventional farm vehicles to have ready access to the pit, thereby enabling the pit to be loaded and unloaded conveniently. The pit is insulated on its sides and bottom and is closed at the top by a heat-insulating cover. The pit is heated to assist the fermentation process. After several days of heating, the pit is drained through a sediment trap and the filtered pit drainage is separated into concentrated ethanol and a mixture of water and enzymes. The solid residue left in the pit is removed for use as feed or fertilizer. The separated water and hydrolyzing agents are stored in a reservoir for subsequent flooding of the pit when a new quantity of carbohydrate-containing material is added to the pit.

8 Claims, 5 Drawing Figures

U.S. Patent   Jul. 26, 1983   Sheet 1 of 2   4,395,488
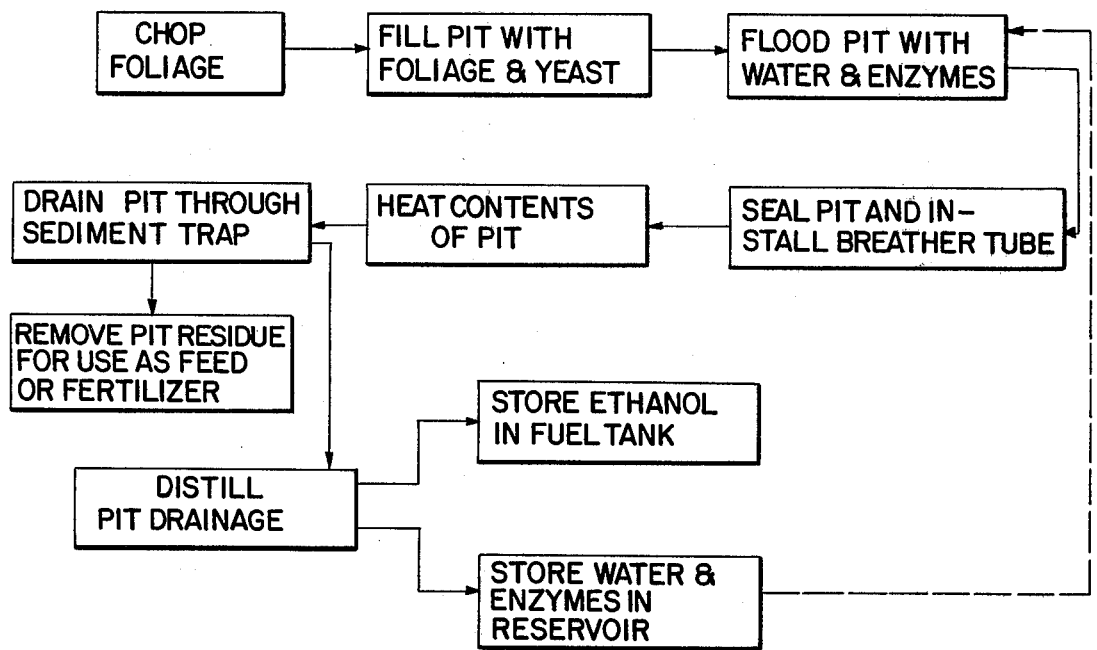
*Fig. 1*
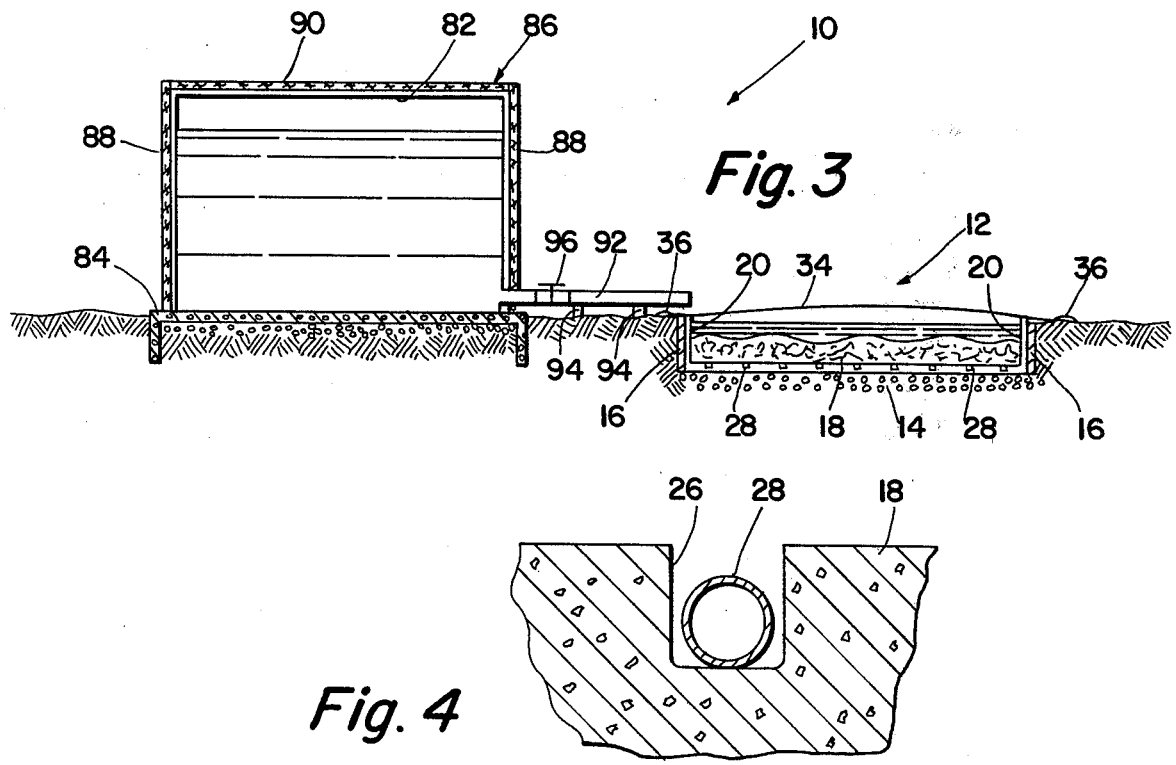
*Fig. 3*
*Fig. 4*

DRIVE-THROUGH PIT PRODUCTION OF ETHANOL

BACKGROUND OF THE INVENTION

1. Field of the Invention

The invention relates to the production of ethanol by the fermentation of carbohydrate-containing materials and, more particularly, to a method and apparatus for producing ethanol in which a drive-through pit is utilized for fermentation.

2. Description of the Prior Art

Ethanol ($C_2H_5OH$), also known as grain alcohol or ethyl alcohol, is a colorless, volatile liquid probably most popularly known as the physiologically active ingredient in alcoholic beverages. Ethanol has been produced for centuries by the fermentation of carbohydrates.

In the fermentation process for the production of ethanol, complex sugar, starch, hemicellulose and cellulose molecules are broken down, or hydrolyzed, into simpler components by the action of acids or enzymes. Enzymes are complex organic compounds that originate in living organisms. The presence of either acids or enzymes acts as a catalyst in the fermentation process.

The production of ethanol from substances such as corn, potatoes, rice, and the like involves first the enzymatic conversion of starch into sugar (glucose) using the enzyme amylase. The sugar then is converted into ethanol and carbon dioxide by the action of zymase, an enzyme produced by living yeast cells. Fermentation must be carried out in dilute water solutions because the yeast cells cannot live and multiply in concentrated sugar or alcohol solutions. The dilute alcohol solutions thus produced can be dehydrated to obtain concentrated solutions of water-free ethanol. Dehydration commonly is carried out by distillation, but it also can be done by the use of semipermeable membranes and chemical dewatering compounds.

The present day production of ethanol is carried out principally by acting upon only the starch-containing (or grain) portion of various crops such as corn, rice, rye, and so forth. Although the starch-containing portion of a plant generally constitutes only a small portion of the overall bulk of the plant, ethanol has been derived almost exclusive only from the starch-containing portion because starches are readily converted to glucose. The remainder of the plant, including its stalk and leaves, largely is made of hemicellulose and cellulose, both of which are relatively difficult to convert to fermentable sugars such as glucose. Hemicellulose is a branched carbohydrate polymer made up pentoses such as xylose, arabinose, and various sugar acids. Cellulose is a complex polymeric carbohydrate which has the same chemical formula as starch, but which has a slightly different molecular arrangement; the crystalline structure structure of cellulose, in combination with a polyphenolic macromolecule known as lignin contained in a plant, acts to seal the cellulose and prevent it from being hydrolyzed. Even though hydrolysis of hemicellulose and cellulose is relatively difficult, both hemicullulose and cellulose, like starch, eventually can be completely converted to fermentable sugars such as glucose and thereafter to ethanol. Reference is made to Ladisch, M.R., *Cellulosic Residues (Biomass) as a Renewable Source of Fuels*, American Society of Agricultural Engineers, presented at the Hyatt Regency Hotel, New Orleans, La., Dec. 11–14, 1979, the disclosure of which is incorporated herein by reference.

While the chemical reactions in the fermentation process for the production of ethanol have been known for some time, and while other processes exist for manufacturing ethanol (such as from ethylene, or as a by-product of hydrocarbon synthesis from carbon monoxide and hydrogen, among other techniques), none of the presently known techniques for manufacturing ethanol have been completely responsive to recent needs. Because of its volatile qualities, ethanol, either mixed with gasoline or used undiluted, can be used to power internal combustion engines. Due to recent shortages of petroleum, there is a great need for ethanol to be produced in quantity. In contrast to the relatively small quantities of ethanol which have been produced for beverages and other purposes, the expected widespread use of ethanol as a fuel for internal combustion engines will require a great increase in the production of ethanol in the near future.

SUMMARY OF THE INVENTION

In response to the foregoing considerations, a new and improved method and apparatus for the manufacture of ethanol employs a drive-through pit into which the entire chopped bulk of carbohydrate-containing materials such as plants can be processed into ethanol by fermentation. The pit is constructed of a liquid-impervious material such as reinforced concrete insulated on its sides and bottom. A network of heating pipes is placed in grooves formed in the bottom of the pit to assist in heating during the fermentation process. The configuration and depth of the pit are such as to permit conventional farm vehicles to have ready access to the pit, thereby enabling the pit to be loaded and unloaded conveniently.

An insulating cover is used to seal the upper surface of the pit during the fermentation process. The cover is constructed of an ultravoilet stabilized plastic film having air bubbles entrapped between layers of a plastic material to provide heat-insulating qualities. The back of the cover is coated with a solar selective coating which absorbs solar radiation to provide additional heat during the daytime.

The pit is slightly deeper at one end than at the other. This is done in order to drain the pit once the fermentation process is completed. The drainage of liquids from the pit occurs through a gate located at the deeper end of the pit. The gate leads to a sediment trap containing a series of screens for filtering solids. Each screen is easily removable from the sediment trap for cleaning.

From the sediment trap, the fermented liquid, or wash, is pumped into a wash storage reservoir. The wash storage reservoir stores the wash until it can be dehydrated into concentrated ethanol. Commercially available distillation equipment is used to dehydrate the wash. The distillate consists of concentrated ethanol of approximately 190 proof (95% ethanol) which is conveyed to a fuel tank for later use as a fuel.

The distilland is a solution containing water and hydrolyzing agents such as enzymes. The water/enzyme solution is stored in a reservoir for subsequent use in another fermentation process. The construction of the water/enzyme storage reseroir and the wash storage reservoir essentially are identical. The outside of each reservoir is painted with a solar selective coating to absorb solar radiation and therefore preheat the contents of the reservoir. The entire outside of each reservoir is encapsulated within an ultraviolet stabilized plastic film. The plastic film is supported by frame members which hold the film several inches from the surface of the reservoir so as to provide a "greenhouse" effect.

By use of the open pit process according to the invention to produce ethanol, the entire bulk of a plant including its stock, leaves, and grain can be processed into ethanol. The process affords several distinct advantages over previous fermentation methods to manufacture ethanol, including the production of more ethanol per acre of land because the entire plant, not just its grain, can be processed. Moreover, the use of conventional farm equipment such as tractors and wagons can be used, thereby reducing the investment required by farmers. The ability to utilize two or more crops per year from the same space of land is made possible, because fully natured crops are not required in the process. Additionally, the pit and the storage reservoirs are very energy-efficient, and much of the energy required by the process is provided by solar heating.

The foregoing, as well as other features and advantages of the invention, are described in the accompanying specification and are illustrated in the accompanying drawings.

DETAILED DESCRIPTION OF THE DRAWINGS

FIG. 1 is a schematic representation of process steps according to the invention;

FIG. 3 is a cross-sectional view of apparatus according to the invention taken along a plane indicated by line 3—3 in FIG. 2;

FIG. 4 is an enlarged cross-sectional view of a heating pipe according to the invention; and, FIG. 5 is a cross-sectional view of a pit according to the invention taken along a plane indicated by line 5—5 in FIG. 2.

DESCRIPTION OF THE PREFERRED EMBODIMENT

Figure 2:
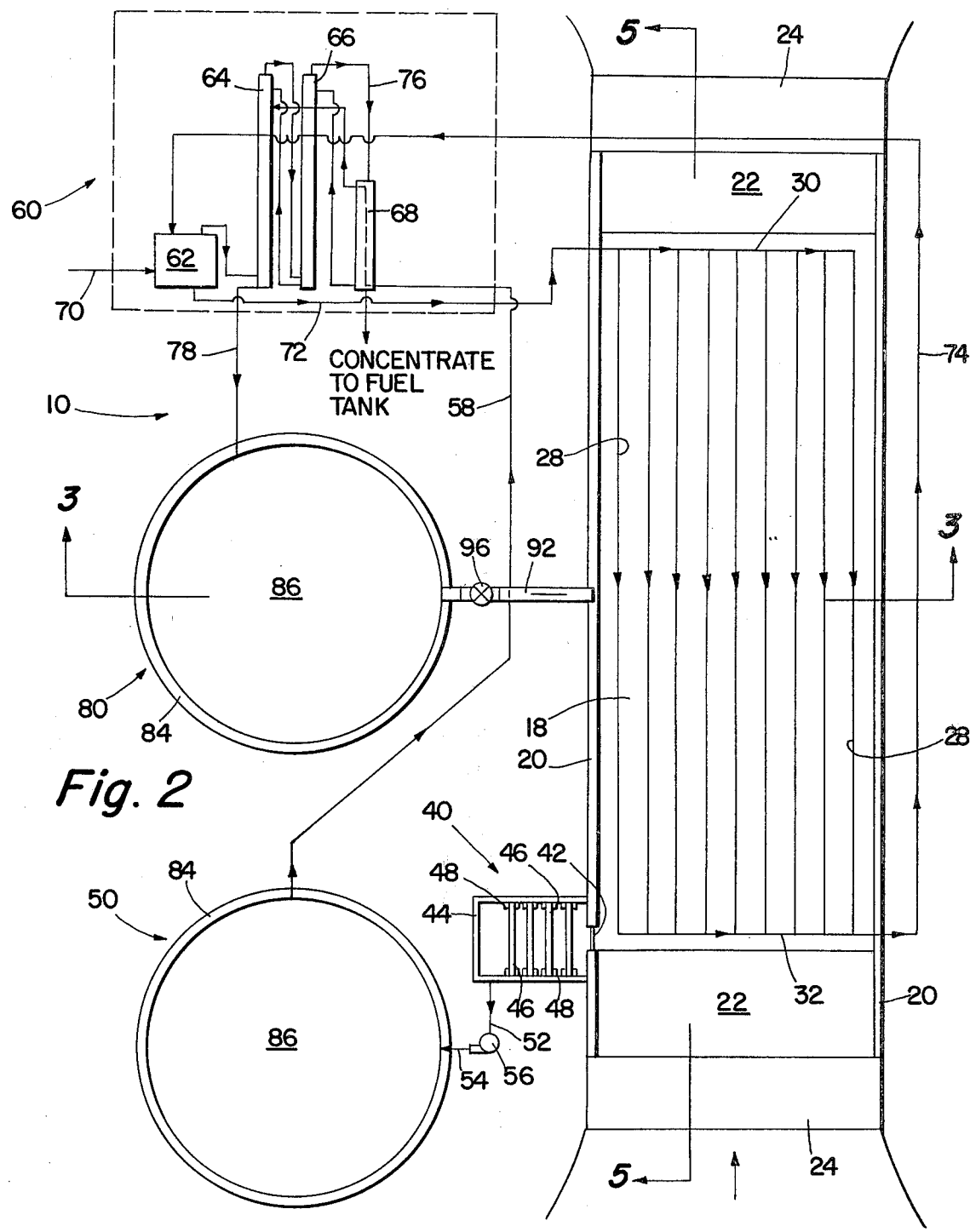
FIG. 2 is a schematic plan view of apparatus included as part of the invention.
Figure 5:
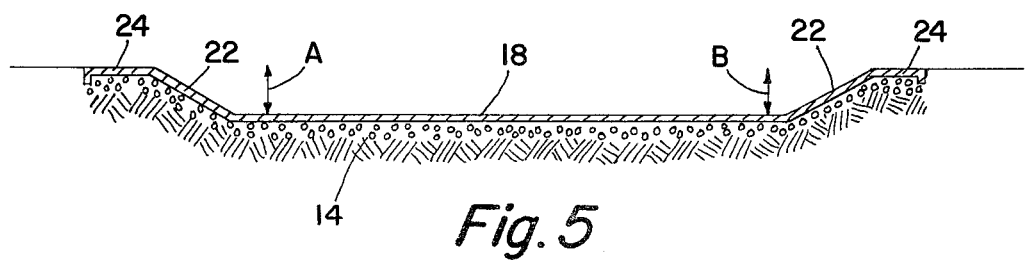

Referring to FIGS. 2-5, apparatus 10 for producing ethanol through the fermentation of carbohydrate-containing substances is shown. The apparatus 10 includes a pit 12 in which material to be fermented is placed, a sediment trap 40 for filtering solid material from ethanol-containing pit drainage, a storage reservoir 50 for storing pit drainage, distillation equipment 60 for separating the pit drainage into connected ethanol and a mixture of water and enzymes, and a storage reservoir 80 for storing the separated water/enzyme mixture for subsequent use in another fermentation process.

The pit 12 is built by forming a generally rectangular opening in the earth. The bottom of the pit 12 is provided with a bed of gravel 14. The sides of the pit 12 (FIG. 3) are insulated with insulating sheets 16 made of expanded synthetic resinous material such as that marketed under the mark STYROFOAM. The remainder of the pit 12 is formed of reinforced concrete having a bottom wall 18, side walls 20, end walls 22 inclined from the horizontal (FIG. 5), and end aprons 24. The end walls 22 and the aprons 24 permit conventional farm machinery such as tractors and wagons to be driven into the pit 12.

The bottom wall 18 includes a plurality of parallel grooves 26 within which heating pipes 28 are disposed. The pipes 28 are made of one-half inch diameter steel tubing which are connected at their ends to a hot water supply manifold 30 and a hot water return manifold 32. The pipes 28 and the manifolds 30, 32 convey heated water so as to heat the contents of the pit 12 and promote the fermentation process. The notches 26 are sufficiently deep that the pipes 28 are below the surface of the bottom wall 18. Accordingly, equipment such as tractors can be driven into the pit 12 without damaging the pipes 28. Also, the pipes 28 cannot be damaged by scraper blades because the pipes 28 are below the surface of the bottom wall 18.

One end of the pit 12 is deeper than the other. This is indicated by the dimension "A" in FIG. 5 and by the dimension "B" in FIG. 5. In a typical application, dimension A is on the order of 3.5 feet, and dimension B is on the order of 2.5 feet. The width of the pit 12 is on the order of 20 feet, and the spacing between adjacent pipes 28 is on the order of two feet. The length of the pit 12 from apron to apron is about 60 feet. In order to sustain the loads which can be expected to be imposed upon the pit 12, the gravel bed 14 is approximately four inches thick, and the bottom wall 18 is approximately six inches thick. The insulating sheets 16 are on the order of four inches thick.

In order to seal the pit 12 during the fermentation, process, a cover 34 is provided. The cover 34 is sealed at the edges of the pit 12 by dirt mounds 36. The cover 34 may be a commercially available swimming pool cover consisting of an ultravoilet stabilized plastic film, air bubbles entrapped between layers of plastic film to provide heat-insulating qualities, and a backing of a solar selective coating to absorb solar radiation and thereby provide additional heat during the daytime. The cover includes a small hose (not shown) for venting the pit 12 as carbon dioxide gas is produced during the fermentation process.

The sediment trap 40 is located adjacent the lower end of the pit 12 at one corner. The sediment trap 40 includes a gate 42 for controlling the discharge of liquids from the pit 12. The sediment trap 40 in the form of a trough-like structure 44. A plurality of screens 46 are placed in the trough 44. The screens 46 are vertically oriented and are supported in spaced location to each other by a plurality of guides 48. The screens 46 can be removed easily from the trough 44 for cleaning. Liquid passing from the pit 12 through the trough 44 also passes through the screens 46, thereby filtering solids from the liquid.

The storage reservoir 50 receives liquid, or wash, drained from the pit 12. The wash is pumped into the reservoir 50 through conduits 52, 54 by means of a pump 56. The reservoir 50 largely is identical to the reservoir 80. A detailed discussion of the reservoir 80 will be set forth subsequently.

From the reservoir 50, the wash is conveyed by gravity through a conduit 58 to the distillation equipment 60. Although the wash can be separated into ethanol and non-ethanol components by the use of semipermeable membranes and chemical dewatering compounds, a distillation process is preferred. The distillation equipment includes commercially available components such as a boiler 62, a first distillation column 64, a second distillation column 66, and a condenser 68. A supply of water is provided for the boiler 62 through a conduit 70. Hot water from the boiler 62 is conveyed to the hot water supply manifold 30 by way of a conduit 72. Water passing through the pipes 28 is returned to the boiler 62 from the hot water return manifold 32 by way of a conduit 74. As has been mentioned already, hot water supplied to the pipes 28 from the boiler 62 serves to heat the pit contents during the fermentation process.

Wash from the storage reservoir 50 is conveyed through the conduit 58 to the condenser 68 where the wash is pre-heated. From the condenser 68, the wash is conveyed to the first distillation column 64 and then to the second distillation column 66. Distilled ethanol is conveyed from the second distillation column 66 to the condenser 68 by way of a conduit 76. Concentrated ethanol discharged from the condenser 68 is conveyed to a fuel tank (not shown) for subsequent use as a fuel. Concentrated wash (distilland from the distillation process) is conveyed to the storage reservoir 80 by way of a conduit 78. The distilland essentially is a mixture of water and hydrolyzing agents such as enzymes. The distilland is usable in subsequent fermentation processes.

The reservoirs 50, 80 are largely identical, and include a cylindrical steel tank 82 having a diameter of approximately 20 feet, a height of approximately 12.5 feet, and a capacity of approximately 30,000 gallons. Each tank 82 is supported atop a concrete platform 84. The outer surface of the tank 82 is painted with a solar selective coating to absorb solar radiation and thereby pre-heat the contents of the tank 82 before distillation or before being returned to the pit 12, as the case may be. The entire outer surface of each tank 82 is encapsulated within an ultraviolet stabilized plastic film 86 supported by spaced structural members 88, 90 which may take the form of two-by-fours. The film 86 is spaced from the outer surface of the tank 82 several inches so as to provide a "greenhouse" effect to assist in heating the contents of the tank 82.

The reservoir 80, but not the reservoir 50, includes a drain pipe 92 extending outwardly of the tank 82 near its bottom. The drain pipe 92 is supported by braces 94 and includes a valve 96 for controlling discharge of the contents of the reservoir 80 through the conduit 92. As can be seen in FIG. 3, the conduit 92 extends slightly over the pit 12 so that the water/enzyme mixture stored in the reservoir 80 can be discharged into the pit 12 when desired.

The apparatus 10 described thus far can produce approximately 5,000 gallons of 190 proof ethanol every three days. The capacity of the apparatus 10 can be increased if an additional pit 12 is provided. The additional pit, identical in construction to the pit 12, could be provided to the left of the reservoirs 50, 80 as viewed in FIG. 2. If an additional pit 12 is employed, the output of the apparatus 10 essentially can be doubled.

OPERATION

The procedure for producing ethanol utilizing the drive-through pit fermentation process according to the invention can be broken down into several steps. Referring to FIG. 1, these steps are:

1. Carbohydrate-containing material such as corn, sugar cane, sorghum, and the like is chopped using conventional farm equipment. This equipment might include a row crop tractor, an ensilage chopper, and one or more wagons. In short, the same farm equipment presently used by farmers to chop silage can be used to chop the carbohydrate-containing material used with the invention.

2. The chopped carbohydrate-containing material is dumped into the pit 12 and packed. Conventional farm equipment such as a tractor and scraper blade are used to spread and pack the chopped material into the pit 12. Yeast is sprinkled in with the material as the pit 12 is filled.

3. The contents of the reservoir 80 are discharged into the pit 12 so as to flood the pit 12 with a dilute solution of enzymes such as amylase and/or hydrolyzing solvents such as mineral acids. Sufficient solution is added to completely cover the contents of the pit with at least six inches of liquid.

4. The top of the pit 12 is sealed with the cover 34 and the dirt mounds 36. The hose included with the cover 34 is placed into the sediment trap 40 to permit carbon dioxide gas to escape during the fermentation process.

5. The contents of the pit 12 are fermented at 120 degrees Fahrenheit for three days. Heat is provided by pumping hot water from the boiler 62 through the manifolds 30, 32 and the conduits 28 located in the bottom wall 18 of the pit 12. Heat also is provided by the thermal characteristics of the cover 34. The insulating materials 14, 16 positioned around the walls 18, 20 of the pit 12 assist in making the heating process more efficient.

6. After fermentation is completed, the gate 42 is opened and the pit 12 is drained into the trough 44. Solids are filtered out of the wash by the screens 46 and the wash is pumped into the wash storage reservoir 50. Drainage of the pit 12 can be speeded by driving a tractor or other vehicle over the contents of the pit 12 and squeezing out the last remaining liquids.

7. The wash is drained from the reservoir 50 and is distilled by the distillation equipment 60 into 190 proof (95%) ethanol. The ethanol is stored in a fuel tank (not shown) and the distilland, consisting essentially of water and enzymes, is pumped into the storage reservoir 80.

8. The solid residue remaining in the pit 12 is removed by using conventional farm equipment such as a tractor and front end loader. The residue either can be fed to livestock or used as fertilizer.

Although the basic chemical reactions employed to produce ethanol according to the invention do not differ from those of fermentation steps employed for many years previously, the method and apparatus according to the invention permits the entire bulk of a plant, including its stock, leaves, and grain, to be processed into ethanol. The method and apparatus according to the invention thereby offers several distinct advantages over methods previously employed to make ethanol. These advantages include the production of more ethanol per acre of land since the entire plant, not just its grain, can be processed into ethanol. Moreover, the use of conventional farm equipment such as tractors and wagons can be used, thereby significantly reducing the investment required by farmers. Additionally, the ability to utilize two or more crops per year from the same piece of land is made possible because fully matured crops are not required in the process. Yet an additional advantage of the method and apparatus according to the invention is that the pit 12 and the reservoirs 50, 80 function as solar collectors, thereby increasing the efficiency of the overall process.

Although a preferred embodiment of the invention has been described in some particularity, it will be appreciated that many variations and modifications in the preferred embodiment may be made without deviating from the invention. Accordingly, it is to be understood that, within the scope of the appended claims, the invention may be practiced otherwise than as specifically described.

What is claimed is:

1. A method for producing ethanol, comprising the steps of:
   depositing carbohydrate-containing material into a pit having a bottom with one end lower than the other and heating pipes within grooves in the bottom below the surface of the bottom;
   driving a vehicle into the pit and using it to spread said carbohydrate-containing material;
   flooding the pit with a mixture of water and hydrolyzing agents until the material is covered with at least six inches of liquid;
   fermenting the contents of the pit;
   draining the liquid contents of the pit from the lower end of the pit;
   separating the drained liquid into concentrated ethanol and a mixture of water and hydrolyzing agents;
   removing the mixture of water and hydrolyzing agents for later use in flooding the pit; and
   driving a vehicle into the pit and removing the solid residue from the pit with the vehicle.

2. The method of claim 1, including the additional steps of covering the pit during the fermentation process with a heat-insulating cover and pumping hot water through said pipes.

3. The method of claim 1, including the additional step of storing the drained liquid contents of the pit in a reservoir prior to the step of separating the drained liquid into concentrated ethanol and a mixture of water and hydolyzing agents.

4. The method of claim 1, wherein the step of separating the drained liquid into concentrated ethanol and a mixture of water and hydrolyzing agents is carried out by distillation, whereby a distillate of concentrated ehtanol and a distilland of water and hydrolyzing agents are formed.

5. Apparatus for producing ethanol by the fermentation of carbohydrate-containing material, comprising:
   a pit into which carbohydrates-containing material can be placed and flooded with a solution for producing ethanol;
   a sediment trap adjacent the pit for draining the pit and removing solids from the drained liquid;
   separation equipment for producing concentrated ethanol and a mixture of water and hydrolyzing agents;
   a storage reservior for storing a mixture of water and hydrolyzing agents for subsequent use in producing ethanol;
   a cover for the pit to seal the pit during the fermentation process;
   said pit including a bottom wall, side walls and sloping end walls;
   said bottom wall being impervious to liquids, the bottom wall being inclined with respect to the horizontal so that one end of the pit is deeper than the other;
   said side walls extending upwardly from the bottom wall, the side walls being impervious to liquids;
   said sloping end walls extending outwardly from the bottom wall at an angle to the horizontal, the end walls being impervious to liquids;
   generally horizontal aprons extending laterally outwardly from the end walls;
   a plurality of grooves formed in the bottom wall;
   heating pipes located in the grooves, the heating pipes adapted to convey heated fluid so that the contents of the pit can be heated;
   said grooves having a depth greater than the diameter of said pipes, whereby a vehicle may be driven over said bottom wall without rupturing said pipes; and
   a drainage gate formed in one of the side walls adjacent the deeper end of the pit.

6. The apparatus of claim 5, additionally including a reservoir for storing drained liquid contents of the pit prior to separation into concentrated ethanol and a mixture of water and hydrolyzing agents.

7. The apparatus of claim 6, wherein the reservoirs are heated with a solar selective coating and are surrounded by a light-transmissive cover spaced a small distance from the surface of the reservoirs.

8. The apparatus of claim 5, wherein the separation equipment is in the form of a boiler, a distillation column, and a condenser.

* * * * *